United States Patent [19]

Nissen et al.

[11] 4,310,705

[45] Jan. 12, 1982

[54] PREPARATION OF HIGHER UNSATURATED KETONES

[75] Inventors: Axel Nissen, Leimen; Gerd Kaibel, Lampertheim; Otto Woerz, Ludwigshafen; Lothar Arnold, Heidelberg; Manfred Braun, Mutterstadt; Walter Rebafka, Eppelheim, all of Fed. Rep. of Germany

[73] Assignee: BASF Aktiengesellschaft, Fed. Rep. of Germany

[21] Appl. No.: 163,401

[22] Filed: Jun. 26, 1980

[30] Foreign Application Priority Data

Jul. 18, 1979 [DE] Fed. Rep. of Germany ....... 2928944

[51] Int. Cl.³ .............................................. C07C 45/48
[52] U.S. Cl. .................................... 568/391; 568/346; 568/398; 568/356
[58] Field of Search ............... 568/391, 398, 347, 346, 568/356

[56] References Cited

U.S. PATENT DOCUMENTS

| 2,795,617 | 6/1957 | Kimel et al. | 568/398 |
| 2,839,579 | 6/1958 | Kimel et al. | 568/398 |
| 3,101,375 | 8/1963 | Crocker | 568/398 |
| 4,173,588 | 11/1979 | Pasedach et al. | 568/391 |

FOREIGN PATENT DOCUMENTS

| 1793445 | 5/1971 | Fed. Rep. of Germany | 568/391 |
| 1219166 | 5/1960 | France | 568/398 |
| 2371441 | 6/1978 | France | 568/391 |
| 52-68115 | 6/1977 | Japan | 568/398 |
| 822572 | 10/1959 | United Kingdom | 568/391 |
| 951927 | 3/1964 | United Kingdom | 568/391 |
| 1463184 | 2/1977 | United Kingdom | 568/391 |

OTHER PUBLICATIONS

Carroll, J. Chem. Soc., 1941, pp. 507–511.

Primary Examiner—G. T. Breitenstein
Assistant Examiner—James H. Reamer
Attorney, Agent, or Firm—Keil & Witherspoon

[57] ABSTRACT

An improved process for the preparation of higher unsaturated ketones, such as geranylacetone and farnesylacetone, by reacting a $\beta,\gamma$-unsaturated alcohol and an alkyl acetoacetate at an elevated temperature in the presence of an organic aluminum compound, with elimination, and removal, of the alcohol derived from the alkyl acetoacetate in a reactor system carrying a fractionating column. The improvement in the purity, yield, and especially space-time yield of the product is achieved by starting from an alcohol having a higher boiling point than that of the alkyl acetoacetate used, carrying out the reaction in the presence of a small amount of an inert liquid which has a boiling point between that of the alkyl acetoacetate and the alcohol to be eliminated therefrom, and ensuring that the temperature at the bottom of the fractionating column is only slightly higher than the boiling point of the added liquid, under the prevailing pressure.

6 Claims, 1 Drawing Figure

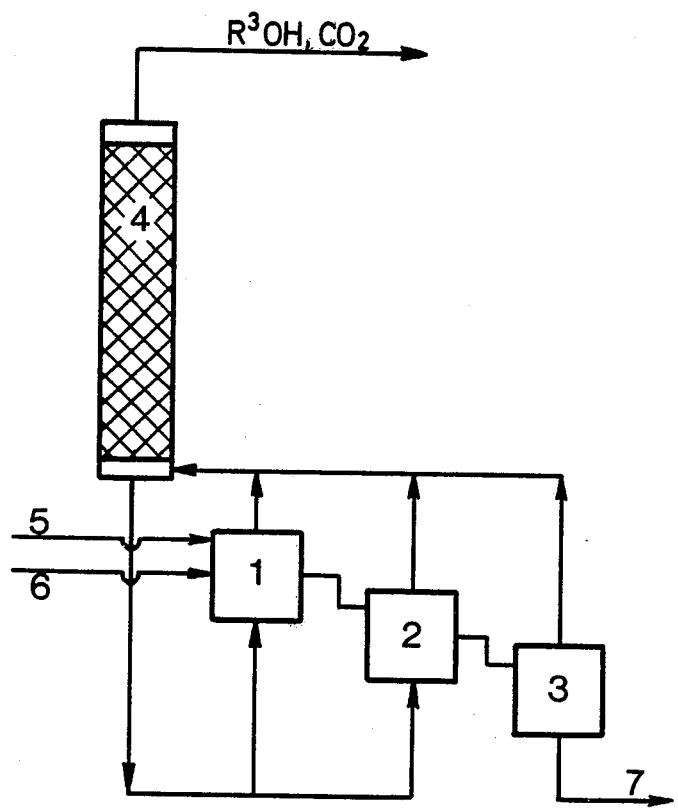

PREPARATION OF HIGHER UNSATURATED KETONES

The present invention relates to an improved process for the preparation of higher unsaturated ketones by reacting a β,γ-unsaturated alcohol with an alkyl acetoacetate at an elevated temperature in the presence of an organic aluminum compound, with elimination and removal of the alcohol derived from the alkyl acetoacetate.

Apart from the improvements according to the invention, the essential characteristic features of this reaction have already been disclosed. Originally, this type of reaction between an unsaturated alcohol and an alkyl acetoacetate was described by Carroll (J. Chem. Soc. (London) 1941, 507–511). A more recent description of the process for preparing 6,10,14-trimethyl-5-pentadecen-2-one is given in French Pat. No. 1,219,166. According to this process, the desired ketone is obtained in 77% yield, the reaction time being about 10 hours.

Unsatisfactory aspects of this process, for industrial operation, are the relatively long reaction time and the inadequate yield. The latter is particularly serious when preparing higher ketones, ie. when using higher alcohols of the formula II, since these become more expensive to prepare with increasing chain length. If attempts are made to improve the yield by using an excess of the cheaper component, in the present case the alkyl acetoacetate, dehydroacetic acid is readily formed as a by-product and is difficult to separate subsequently from the desired product and furthermore may block the outlet lines of the columns used for the purification process.

There are a number of other Patents which describe the various embodiments of this Carroll reaction. For example, German Pat. No. 1,068,696 states that it may be advantageous to carry out the reaction in the presence of a solvent. U.S. Pat. No. 2,795,617 and German Published Application DAS No. 1,053,498 state that the presence of a solvent is "possible, but normally neither necessary nor desirable". In all cases where the use of a solvent is mentioned, high-boiling solvents are named, with boiling points far above the reaction temperature, eg. decalin (boiling point 193° C.), tetralin (boiling point 207° C.), diphenyl ether (boiling point 259° C.), silicone oil and high-boiling mineral oils.

However, the use of these high-boiling solvents or diluents in general does not produce any substantial improvement in the yield of ketone.

It is an object of the present invention to improve the above process so that the higher unsaturated ketones, especially the ketones which are sought after as scents and as intermediates for isophytol, for example geranylacetone, farnesylacetone, 6,10-dimethyl-5-undecen-2-one and 6,10,14-trimethyl-5-pentadecen-2-one, can be prepared in higher yields and with higher space-time yields.

We have found that this object is achieved and that the unsaturated ketones of the general formula I

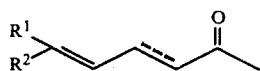

where the broken line may denote an additional C—C bond, $R^1$ is alkyl of 1 to 4 carbon atoms, preferably $CH_3$, and $R^2$ is saturated or unsaturated alkyl, cycloalkyl or cycloalkylalkyl of 4 to 30 carbon atoms, preferably a group

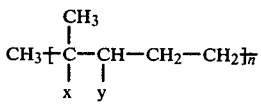

where n is an integer from 1 to 6 and x and y are both H, or x is methoxy and y is H, or x and y together are an additional bond between the carbon atoms shown as carrying x and y, are obtained in substantially better yields and with substantially better space-time yields by reacting an unsaturated alcohol of the general formula II

 (II)

with an alkyl acetoacetate of the general formula III

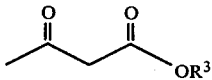 (III)

where $R^3$ is alkyl of 1 to 4 carbon atoms, at an elevated temperature in the presence of an organic aluminum compound, with elimination and continuous distillative removal of an alcohol of the general formula IV $R^3$—OH (IV)

in a reactor system carrying a fractionating column, if

A. the unsaturated alcohol of the formula II which is used has a boiling point higher than that of the alkyl acetoacetate used, B. the reaction is carried out in the presence of from 0.5 to 100% by weight, based on the alcohol of the formula II, of a liquid which is inert under the reaction conditions or which cannot undergo any undesirable side-reactions and which has a boiling point between that of the alkyl acetoacetate starting material of the general formula III and the alcohol of the general formula IV to be eliminated therefrom, and C. steps are taken to ensure that the temperature at the bottom of the fractionating column is not more than 40° C., preferably not more than 20° C., higher than the boiling point of the added liquid, under the prevailing pressure.

The process according to the invention proves particularly advantageous if an aliphatic ketone of 4 to 7 carbon atoms is used as the inert compound according to the above definition and if the alkyl acetoacetate used is methyl acetoacetate, ethyl acetoacetate or isopropyl acetoacetate. The process is of particular importance for preparing ketones of the general formula I, where $R^1$ is $CH_3$ and $R^2$ is a group of the general formula

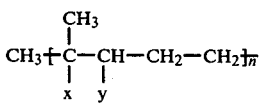

where n is an integer from 1 to 6, and x and y are both H, or x is methoxy and y is H, or x and y together are an additional bond between the carbon atoms shown as carrying x and y.

In a further particularly advantageous embodiment of the novel process, the reaction is carried out in the presence of 3-methyl-but-1-en-3-ol, and a reaction of this compound with the alkyl acetoacetate additionally takes place, as a desired side-reaction, giving 2-methyl-hept-2-en-6-one as an additional useful product.

It is an important aspect that the high yields achievable according to the invention are coupled with virtually quantitative conversion, based on all the starting materials, even if only a slight excess, if any, of one of the components is employed. It is also noteworthy that by employing the measures according to the invention the space-time yield can be increased by a factor of 2-3.

According to the invention, the liquids employed, which are inert under the reaction conditions or cannot undergo an undesirable side-reaction, have a boiling point between that of the alkyl acetoacetate employed, of the formula III, and the eliminated alcohol IV, ie. they are liquids which under atmospheric pressure generally boil at from 60° to 180° C., preferably from 80° to 150° C. and especially from 90° to 120° C. Examples of suitable compounds are alcohols, esters, ethers, halohydrocarbons and aromatic hydrocarbons of appropriate boiling point, but preferably aliphatic ketones, and especially those of 4 to 7 carbon atoms. Specific examples of suitable compounds are isobutanol, 3-methyl-but-1-en-3-ol, butyl formate, butyl acetate, toluene, o-xylene, m-xylene, p-xylene, ethylbenzene, 1,1,2-trichloroethane, trichlorofluoroethane, 1,4-dioxane, butan-2-one, 3-methyl-butan-2-one, pentan-3-one and heptan-2-one, especially butan-2-one, 3-methyl-butan-2-one and pentan-3-one. In the text which follows, these liquids will, for brevity, be referred to as intermediate-boiling liquids.

The intermediate-boiling liquids should advantageously not form an azeotrope with the alcohol of the formula IV eliminated during the reaction, eg. with methanol, ethanol and isopropanol. This proviso is however only important with regard to the recoverability of the intermediate-boiling liquid and has no particular advantageous effect on the reaction.

The intermediate-boiling liquid is in general used in an amount of from 0.5 to 100% by weight, based on the alcohol of the formula II, and is advantageously selected so that only from about 1 to 20% by weight, based on the said alcohol, are required. This is the case if the intermediate-boiling liquid boils as low as is possible whilst still ensuring that it is easily separable from the alcohol $R^3OH$. The closer the boiling point of the intermediate-boiling liquid is to that of the alkyl acetoacetate, the more of the said liquid is required, which obviously makes the reaction less advantageous overall.

If a liquid which is not inert under the reaction conditions, but undergoes a desired side-reaction, is used as the intermediate-boiling liquid, it is of course necessary constantly to add to the reaction mixture additional amounts of this liquid, corresponding to the amounts consumed by the side-reaction. An example of this embodiment of the process according to the invention is the reaction of linalool, 3,7-dimethyl-oct-1-en-3-ol or 3,7,11-trimethyl-dodec-1-en-3-ol, in which, in addition to geranylacetone, 6,10-dimethyl-undec-5-en-2-one and 6,10,14-trimethyl-pentadec-5-en-2-one respectively, 2-methyl-hept-2-en-6-one, a sought-after intermediate for vitamin A and vitamin E, is obtained with very good selectivity. In this instance, the 3-methyl-but-1-en-3-ol serves both as the intermediate-boiling liquid and as the compound which reacts with the alkyl acetoacetate. Hence, the total amount employed corresponds to the amount required as the intermediate-boiling liquid plus that required as the reactant. In this way, surprisingly, the advantages of the process improvement according to the invention can be utilized indirectly even for the reaction of 3-methyl-but-1-en-3-ol with an alkyl acetoacetate, whilst such utilization of the advantages would otherwise not have been possible, because of the low boiling point of this particular alcohol.

In general, the reaction according to the invention is carried out under atmospheric pressure. However, an intermediate-boiling liquid suitable for use under atmospheric pressure as a rule also performs its function under reduced pressure, ie. in most cases its boiling point under reduced pressure is also intermediate between the corresponding boiling points of the alcohol IV and the alkyl acetoacetate. In certain cases it can be of advantage to carry out the reaction under reduced pressure. In that case, the pressure range must be selected so that the requisite reaction temperature (in most cases 120°-200° C., preferably 140°-170° C.) can be maintained but at the same time the eliminated alcohol of the formula IV can be efficiently separated from the other components present in the reaction mixture and from the intermediate-boiling liquid.

The process of the invention can in principle be applied to all the conventional embodiments of the Carroll reaction, in which the unsaturated alcohol employed boils at a higher temperature than the alkyl acetoacetate employed. However, the process is particularly important for the synthesis of those ketones which are required for the preparation of isophytol, eg. geranylacetone and farnesylacetone.

Accordingly, the novel process is of particular interest for the reaction of an alcohol of the general formula IIa

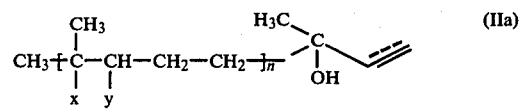

where x, y and n have the abovementioned meanings, for example linalool, 3,7-dimethyl-oct-1-en-3-ol, nerolidol and 3,7,11-trimethyl-dodec-1-en-3-ol.

In principle, the reaction can be carried out with any alkyl acetoacetate, but the methyl ester, ethyl ester and isopropyl ester are preferred not only for economic reasons but also for technological reasons, since the alcohols to be eliminated from these esters are particularly low-boiling and hence are easily removable from the reaction mixture.

Suitable organic aluminum compounds for use in the process according to the invention are compounds of the general formula

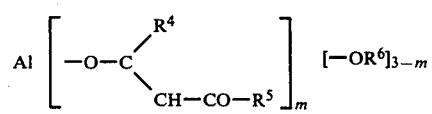

where $R^4$ and $R^5$ are alkyl or alkoxy of 1 to 4 carbon atoms, preferably methyl or ethyl, $R^6$ is alkyl of 1 to 4 carbon atoms and m is 0, 1, 2 or 3, as well as aluminum tri-aryloxylates. The former are, accordingly, lower aluminum trialcoholates, eg. aluminum trimethylate, triethylate, triisopropylate and tri-sec.-butylate, and compounds which are formed on reaction of the said aluminum trialcoholates with stoichiometric amounts of acetylacetonate, alkyl acetoacetate or alkyl malonate, with elimination of alcohol. Examples are aluminum triacetoacetate, aluminum triacetylacetonate, aluminum monoacetoacetatediethylate, aluminum diacetoacetate monoethylate, aluminum monoacetoacetate diisopropylate and aluminum diacetoacetate monoisopropylate. The use of the aluminum trialcoholates, especially of aluminum triisopropylate, is preferred.

Aluminum triaryloxylates are the aluminum salts of aromatic hydroxy compounds, eg. aluminum triphenolate, aluminum tricresolates, aluminum trixylenolates and aluminum trinaphtholates, of which the aryl radicals can also be substituted by lower alkyl or alkoxy, ie. of 1 to 4 carbon atoms, by hydroxyl or by phenyl. Aluminum triphenolate, which is relatively easily obtainable, is particularly advantageous to use.

The amount of the aluminum compound is in general chosen so that its concentration in the reaction mixture does not fall below a value corresponding to 0.05% by weight of Al and does not initially exceed a value corresponding to 6% by weight of Al. Based on alkyl acetoacetate to be converted, about 0.5–5% by weight of aluminum compound are generally required. In the case of aluminum triisopropylate, the preferred compound, the amounts used are, for example, from about 1 to 3% by weight, based on alkyl acetoacetate to be converted.

The process according to the invention can be carried out batchwise or continuously.

When the reaction is carried out batchwise, it is advantageous initially to introduce the unsaturated alcohol of the formula II into the reactor, if possible together with the intermediate-boiling liquid, and with or without the aluminum compound used as the catalyst. After bringing this charge to the desired reaction temperature, the alkyl acetoacetate of the formula III is run in over from about 2 to 4 hours. If quantitative conversion is desired, it is advantageous to keep the reaction mixture at the reaction temperature for about a further 1–2 hours after all the ester has been run in. The progress of the reaction can be followed by observing the evolution of carbon dioxide and/or the amount of alkanol eliminated from the alkyl acetoacetate. The concentration of the alkyl acetoacetate in the reaction mixture can be determined by gas-chromatographic analysis.

It is however also possible initially to introduce into the reactor, in place of the alcohol of the formula II, the alkyl acetoacetate of the formula III, or a mixture of the latter with the alcohol or with the intermediate-boiling liquid, and it is also possible to use a feed of a mixture of compounds II and III.

A suitable reactor system is a conventional heated distillation vessel fitted with a fractionating column, for example a column having from about 2 to 40 theoretical plates. According to the invention, the temperature on the lowest 1–3 theoretical plates of the column should be very close to the boiling point of the intermediate-boiling liquid at the particular pressure employed. If the bottom of the column is set to a higher temperature, the effect achieved by the novel process only diminishes slightly. If on the other hand the temperature at the bottom of the column is reduced to the point of approaching the boiling point of the alcohol IV, the effect achieved according to the invention is greatly diminished. The temperatures in the reaction system are regulated by the dosage rate of the intermediate-boiling liquid.

If the reaction is carried out continuously, the reactor system used can be, for example, a heated kettle cascade comprising from 1 to 10, advantageously from 2 to 4, kettles, the individual kettles being connected to one another by an overflow. It is possible to employ a separate column for each kettle, or only one column for the whole cascade. The material discharged from the bottom tray of the column, which essentially contains the intermediate-boiling liquid, is distributed over the kettles in order to regulate their temperature. The feed, consisting of the compounds of the formulae II and III, with or without the aluminum catalyst, is run continuously into the first kettle. The temperature is regulated by addition of the intermediate-boiling liquid.

As regards the temperatures and pressure to be maintaned, the same remarks apply as for the batchwise procedure.

Using the process improved in accordance with the invention, it is possible to prepare numerous higher ketones, especially those which are required for the preparation of isophytol and hence for the preparation of vitamin E, for example geranylacetone and farnesylacetone, under conditions of virtually quantitative conversion, in very high yields and space-time yields and in high purity.

EXAMPLE 1

Preparation of geranylacetone

A. The apparatus used was a 4 liter flask fitted with a column of about 20 theoretical plates. The column carried thermometers located at regular intervals, so that the temperature could be measured at the bottom and top of the column and also at about each 3rd or 4th theoretical plate.

A mixture of 616 g (4 moles) of linalool, 10 g of aluminum tri-sec.-butylate and 80 g of 3-methyl-butan-2-one (boiling point: 95° C.) was initially introduced into the flask and heated to 165° C. In the course of 4 hours, 464 g (4 moles) of methyl acetoacetate were added dropwise to this mixture; $CO_2$ was evolved and methanol was distilled off at the top of the column. The temperature at the 2nd theoretical plate from the bottom was kept at 90°–100° C. During the reaction, a further 20 g of 3-methyl-butan-2-one were fed in at a rate such as to keep the reaction mixture constantly boiling at 165° C. After completion of the addition of the methyl acetoacetate, the reaction mixture was kept at 165° C. for a further hour, after which no further $CO_2$ was formed. The conversion of methyl acetoacetate was quantitative and geranylacetone was obtained with a selectivity of 94.2%, based on linalool, and of 87.2%, based on methyl acetoacetate.

B. Comparative Experiment

On following the procedure described under A, but without the addition of 3-methyl-butan-2-one, it was necessary, after having completed the dropwise addition of the methyl acetoacetate, to heat the reaction mixture for a further 12 hours, until the evolution of $CO_2$ ceased. The conversion of methyl acetoacetate was 97% and geranylacetone was obtained with a selectivity of 87%, based on linalool, and 80.2%, based on methyl acetoacetate.

EXAMPLE 2

Preparation of 6,10-dimethyl-undec-5-en-2-one

A mixture of 624 g (4 moles) of 3,7-dimethyl-oct-1-en-3-ol, 8.5 g of aluminum triisopropylate and 70 g of pentan-3-one (boiling point 101.7° C.) was heated to 165° C. in the apparatus described in Example 1. 464 g (4 moles) of methyl acetoacetate were then added dropwise in the course of 4 hours. The temperature at the 2nd theoretical plate from the bottom was kept at 100°–110° C. During the reaction, a further 20 g of pentan-3-one were added at a rate such that the reaction mixture constantly boiled at 165° C. After the methyl acetoacetate had been added, heating of the reaction mixture was continued until the evolution of $CO_2$ had ceased, which required about 1 hour. Conversion of the methyl acetoacetate was quantitative and the selectivity of 6,10-dimethyl-undec-5-en-2-one was 96.5%, based on 3,7-dimethyl-oct-1-en-3-ol, and 91.1%, based on methyl acetoacetate.

Comparative Experiment (Reaction in the presence of a high-boiling solvent)

A mixture of 624 g (4 moles) of 3,7-dimethyl-oct-1-en-3-ol, 18.5 g of Al isopropylate and 180 ml of isophorone (boiling point 215°–216° C.) was introduced into the apparatus described in Example 1 and 464 g (4 moles) of methyl acetoacetate were added dropwise over 6 hours. The methanol and $CO_2$ formed in the course thereof were taken off at the top of the column. After all the methyl acetoacetate had been added, 22% of unconverted 3,7-dimethyl-oct-1-en-3-ol remained in the flask.

The reaction mixture was therefore kept at 165° C. for a further 4 hours, at which stage no more $CO_2$ was formed. The concentration of starting compound had then fallen to 7%. Distillation of the material discharged from the reactor gave 577 g of 6,10-dimethyl-undec-5-en-2-one. For a conversion of about 90%, this corresponds to a selectivity of 89%, based on 3,7-dimethyl-oct-1-en-3-ol, or 79%, based on methyl acetoacetate.

EXAMPLE 3

Preparation of farnesylacetone

A. A mixture of 888 g (4 moles) of nerolidol, 10 g of aluminum tri-sec.-butylate and 100 g of 3-methyl-butan-2-one was heated to 165° C. in the apparatus described in Example 1. 464 g (4 moles) of methyl acetoacetate were then added dropwise to this mixture in the course of 3 hours. The temperature at the second theoretical plate from the bottom was kept at 90°–100° C. During the reaction, a further 30 g of 3-methyl-butan-2-one were added at a rate such that the reaction mixture constantly boiled at 165° C. After the methyl acetoacetate had been added, the reaction mixture was heated for a further hour, after which no further $CO_2$ was formed. Conversion of the methyl acetoacetate was quantitative and farnesylacetone was obtained with a selectivity of 93.2%, based on nerolidol, and 85.0%, based on methyl acetoacetate.

B. Comparative Experiment

Following the procedure described under A, but without the addition of 3-methyl-butan-2-one, it was necessary, after having completed the dropwise addition of the methyl acetoacetate, to heat the reaction mixture for a further 8 hours, until the evolution of $CO_2$ ceased. Farnesylacetone was hereby obtained with a selectivity of 80.8%, based on nerolidol, and 72.7%, based on methyl acetoacetate. The conversion of methyl acetoacetate was 98%.

EXAMPLE 4

Preparation of 6,10,14-trimethyl-pentadec-5-en-2-one

A mixture of 904 g (4 moles) of 3,7,11-trimethyl-dodec-1-en-3-ol, 8.5 g of aluminum tri-isopropylate and 100 g of pentan-3-one was heated to 165° C. in the apparatus described in Example 1. 464 g of methyl acetoacetate were added dropwise to this mixture in the course of 4 hours. The temperature at the 2nd theoretical plate from the bottom was kept at 100°–110° C. During the reaction, a further 25 g of pentan-3-one were added at a rate such that the reaction mixture constantly boiled at 165° C. After the methyl acetoacetate had been added, heating of the reaction mixture was continued for 1 hour, at which stage the evolution of $CO_2$ had ceased. The conversion of methyl acetoacetate was quantitative and the selectivity of 6,10,14-trimethyl-pentadec-5-en-2-one was 96.3%, based on 3,7,11-trimethyl-dodec-1-en-3-ol, and 91.0%, based on methyl acetoacetate.

EXAMPLES 5 to 11

The apparatus used was a 4 liter flask carrying a column and two dropping funnels. The column had about 20–30 theoretical plates. It was possible to measure the temperature in the distillation vessel and also at about each 4th or 5th theoretical plate over the entire length of the column.

The temperature in the apparatus was regulated by employing a constant heat input (ie., for example, a constant oilbath temperature) and varying the reaction temperature in the vessel by appropriate control of the addition of the intermediate-boiling liquid. The take-off at the top of the column was regulated by varying the temperature at the 8th theoretical plate from the bottom. This temperature was set so that the temperature at the 4th theoretical plate from the bottom corresponded to the boiling point of the intermediate-boiling liquid under atmospheric pressure, whilst the temperature at the top of the column roughly corresponded to the boiling point of methanol. The latter is initially somewhat below 65° C., because of the partial pressure of the $CO_2$ which is eliminated.

The reaction was carried out by initially introducing the unsaturated alcohol together with the aluminum triisopropylate catalyst and then adding the methyl acetoacetate (MAA) dropwise over a certain period $t_z$, for example over 4 hours. Thereafter—except in the Comparative Examples—the reaction had to be continued for a further period $t_N$ of from 1 to at most 2 hours in order to achieve quantitative conversion of MAA and of the allyl acetoacetate intermediate; complete conversion is most simply recognized from the fact that no further $CO_2$ is formed. Since in any case there is virtually no further methanol produced during this final period, the bottom temperature was maintained by heating, and as a result the column temperature profile collapsed over the last half-hour.

The Table which follows summarizes the reaction conditions and the experimental results.

The following abbreviations are used in the Table:
MAA = methyl acetoacetate
HLIN = 3,7-dimethyl-oct-1-en-3-ol (dihydrolinalool)
HDHL = 3,7-dimethyl-oct-1-yn-3-ol
MDHL = 3,7-dimethyl-7-methoxy-oct-1-yn-3-ol
$t_z + t_N$ = addition time + finishing time The molar ratio, shown in the Table, of the starting materials, ie. of the alcohol II and the MAA, was calculated tel quel. In doing this, two effects offset one another. The MAA employed was ~99% pure but the alcohol employed was only from about 93 to 97% pure. Since, however, the yield based on MAA is somewhat less good, the MAA was completely consumed in the reaction, whilst about 2–3% of the alcohol were left. After all the MAA had been run in, the MAA concentration was about 2–3% by weight.

The selectivities, on the other hand, are not based on the alcohol II tel quel, but are converted to relate to 100% pure material, in order to provide a better comparison of the experiments with one another.

| No. | Alcohol II | Molar ratio Alcohol II/ MAA | Al isopropylate [mole %] based on alcohol II | Intermediate-boiling liquid | Reaction time $t_Z + t_N$ [h] | Column temperature$^{(+)}$ [°C.] | Reaction temperature [°C.] | Selectivity based on MAA [%] | Selectivity based on alcohol II [%] |
|---|---|---|---|---|---|---|---|---|---|
| 5 | HLIN | 1:1 | 1.0 | ⟋⟍OH | 6 + 7 | 105 | 165 | 76.8 | 95.7 |
| 6 | HLIN | 1:1 | 1.0 | ⟋⟍O—C(=O)— | 6 + 3 | 90 | 165 | 86.1 | 94.8 |
| 7 | HLIN | 1:1 | 1.0 | C$_6$H$_5$—CH$_3$ | 6 + 2 | 100 | 165 | 86.5 | 92.7 |
| 8 | HLIN | 1:1 | 1.0 | CH$_3$-C$_6$H$_4$-CH$_3$ | 6 + 2 | 130 | 165 | 87.0 | 91.5 |
| 9 | HLIN | 1:1 | 1.0 | isophorone | 4 + 8 | 60 | 165 | 83.2 | 89.3 |
| 10 | HDHL | 1:1 | 1.0 | methyl ketone | 5 + 6 | 100 | 175 | 60.8 | 70.2 |
| 11 | MDHL | 1:1 | 1.0 | ethyl ketone | 5 + 6 | 100 | 175 | 29.2 | 38.2 |

$^{(+)}$Temperature in the column at the 2nd theoretical plate from the bottom

EXAMPLE 12

Combined prepared of 6,10-dimethyl-undec-5-en-2-one and 2-methyl-hept-2-en-6-one The apparatus used was a 2 liter flask carrying a fractionating column having about 20 theoretical plates. The column was fitted with thermometers at regular intervals so that the temperature could be measured at the top and bottom of the column and at about every 4th theoretical plate.

A mixture of 637 g of 3,7-dimethyl-oct-1-en-3-ol, 8.6 g of Al isopropylate, 36 g of methyl acetoacetate and 78 g of 3-methyl-but-1-en-3-ol was heated to 165° C. and 642 g of methyl acetoacetate and 161 g of 3-methyl-but-1-en-3-ol were added dropwise in the course of 5 hours. The temperature at the 2nd theoretical plate was kept at 90°–100° C. by appropriately adjusting the reflux ratio.

The methanol and $CO_2$ formed were distilled off at the top of the column.

After completion of the addition of the components, the reaction mixture was kept at 165° C. for a further 3 hours, by which time the evolution of $CO_2$ had ceased and the methyl acetoacetate employed had been quantitatively converted. Working up by distillation gave 701 g of 6,10-dimethyl-undec-5-en-2-one and 216 g of 2-methyl-hept-2-en-6-one. This corresponds to a selectivity of 95.5%, based on 3,7-dimethyl-oct-1-en-3-ol, of 94%, based on 3-methyl-but-1-en-3-ol and of 90%, based on methyl acetoacetate.

EXAMPLE 13

Combined preparation of 6,10,14-trimethyl-pentadec-5-en-2-one and 2-methyl-hept-2-en-6-one A mixture of 637 g of 3,7,11-trimethyl-dodec-1-en-3-ol (86% pure), 8.6 g of Al isopropylate and 60 g of 3-methyl-but-1-en-3-ol was heated to 165° C. in the apparatus described in Example 12, and 471 g of methyl acetoacetate and 159 g of 3-methyl-but-1-en-3-ol were added dropwise in the course of 5 hours, whilst keeping the temperature at the 2nd theoretical plate of the column at about 90°–100° C. by appropriate adjustment of the reflux ratio. After a further 2 hours' reaction at 165° C., the mixture was worked up by distillation. 598 g of 6,10,14-trimethyl-pentadec-5-en-2-one and 161 g of 2-methyl-hept-2-en-6-one were obtained.

This corresponds to a selectivity of about 94%, based on 3,7,11-trimethyl-dodec-1-en-3-ol, of about 96%, based on 3-methyl-but-1-en-3-ol, and of 87%, based on methyl acetoacetate.

EXAMPLE 14

Combined preparation of geranylacetone and 2-methyl-hept-2-en-6-one

A mixture of 637 g of linalool (91% pure), 36 g of methyl acetoacetate, 6 g of 3-methyl-but-1-en-3-ol and 8.6 g of aluminum isopropylate was heated to 165° C. in the apparatus described in Example 12, and 642 g of methyl acetoacetate and 211 g of 3-methyl-but-1-en-3-ol were added dropwise in the course of 10 hours whilst maintaining a reaction temperature of 165° C., the temperature at the 2nd theoretical plate being kept at about 100° C. After a further 4 hours' reaction time at 165° C., the mixture was worked up by distillation. 681 g of geranylacetone, 212 g of 2-methyl-hept-2-en-6-one and 37 g of unconverted 3-methyl-but-1-en-3-ol were obtained. The selectivities achieved are accordingly as follows: 87% based on 3-methyl-but-1-en-3-ol, 94%, based on linalool, and 88% based on methyl acetoacetate.

EXAMPLE 15

Continuous preparation of geranylacetone

For carrying out the reaction continuously, the reactor system consisted of a kettle cascade, comprising 3 flasks, 1, 2 and 3, each of one liter capacity, joined to one another by an overflow; the flasks are shown diagrammatically in the attached drawing. The vapors from the reaction vessels were conjointly led into the lower hood of the column 4; this column had about 20 theoretical plates. The fresh feed 5, consisting of a mixture of 1 mole of methyl acetoacetate, 1 mole of linalool and 2.1 g of aluminum triisopropylate, was introduced into the first flask at a rate of 300 ml/hour. The intermediate-boiling liquid 6, in the present case 3-methyl-prop-1-an-2-one, was introduced into the first flask when starting up the reaction. Methanol and $CO_2$ were taken off at the top of the column. The material discharged from the column, at the level of the lowest theoretical plate, was divided into two streams which were recycled respectively to the first and second flasks. 3-Methyl-propan-2-one was introduced, as required, into this recycled material, to serve as the intermediate-boiling liquid 6 and to allow a temperature of 165° C. to be maintained in all 3 flasks, accompanied by vigorous boiling. The concentration of 3-methyl-butan-2-one (as determined by gas chromatography) in the flasks stabilized at a value of 4–6% by weight.

The temperature at the 2nd theoretical plate from the bottom of the column was kept at 90°–100° C. These conditions gave a conversion of about 99.9%, based on methyl acetoacetate, and a selectivity of geranylacetone of 95.1%, based on linalool, and of 89.2%, based on methyl acetoacetate.

We claim:

1. A process for the preparation of unsaturated ketones of the formula I

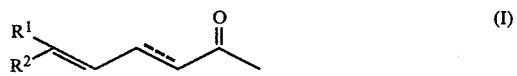

where the broken line may denote an additional C—C bond, $R^1$ is alkyl of 1 to 4 carbon atoms and $R^2$ is saturated or unsaturated alkyl, cycloalkyl or cycloalkylalkyl of 4 to 30 carbon atoms or a group of the formula

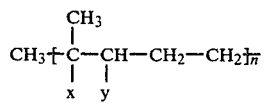

where n is an integer of from 1 to 6, x is methoxy and y is H, which process comprises reacting an unsaturated alcohol of the formula II

with an alkyl acetoacetate of the formula III

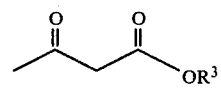

where $R^3$ is alkyl of 1 to 4 carbon atoms, at an elevated temperature in the presence of an organic aluminum compound, with elimination and continuous distillative removal of an alcohol of the formula IV

in a reactor system carrying a fractionating column, wherein

A. the unsaturated alcohol of the formula II which is used has a boiling point higher than that of the alkyl acetoacetate used,
B. the reaction is carried out in the presence of from 0.5 to 100% by weight, based on the alcohol of the formula II, of a liquid which is inert under the reaction conditions or which cannot undergo any undesirable side-reactions and which has a boiling point between that of the alkyl acetoacetate starting material of the general formula III and the alcohol of the general formula IV to be eliminated therefrom, and
C. steps are taken to ensure that the temperature at the bottom of the fractionating column is not more than 40° C. higher than the boiling point of the added liquid, under the prevailing pressure.

2. The process of claim 1, wherein the reaction is carried out in the presence of a ketone of 4 to 7 carbon atoms as the liquid which is inert under the reaction conditions.

3. The process of claim 1, wherein the temperature at the bottom of the fractionating column is not more than 20° C. above the boiling point of the added liquid, under the prevailing pressure.

4. The process of claim 1, wherein the alkyl acetoacetate used is methyl acetoacetate, ethyl acetoacetate or isopropyl acetoacetate.

5. A process as claimed in claim 1, wherein the unsaturated alcohol of the general formula II is a compound where $R^1$ is $CH_3$ and $R^2$ is a group of the formula

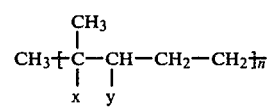

where n is an integer from 1 to 6 and x and y are both H, or x is methoxy and y is H, or x and y together are an additional bond between the carbon atoms shown as carrying x and y.

6. The process of claim 1, wherein the reaction is carried out in the presence of 3-methyl-but-1-en-3-ol as the liquid defined under B.

* * * * *